(12) United States Patent
Liu et al.

(10) Patent No.: US 12,023,493 B2
(45) Date of Patent: Jul. 2, 2024

(54) CLOSED-LOOP SPINAL CORD ELECTRICAL STIMULATION SYSTEM

(71) Applicant: SOOCHOW UNIVERSITY, Suzhou (CN)

(72) Inventors: Yaobo Liu, Suzhou (CN); Dan Yang, Suzhou (CN); Wei Yang, Suzhou (CN); Kai Zhou, Suzhou (CN); Wei Wei, Suzhou (CN); Hui Zhang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 367 days.

(21) Appl. No.: 17/606,427

(22) PCT Filed: Jan. 9, 2020

(86) PCT No.: PCT/CN2020/071041
§ 371 (c)(1),
(2) Date: Oct. 25, 2021

(87) PCT Pub. No.: WO2021/036165
PCT Pub. Date: Mar. 4, 2021

(65) Prior Publication Data
US 2022/0212003 A1    Jul. 7, 2022

(30) Foreign Application Priority Data

Aug. 29, 2019    (CN) .......................... 201910809342.0

(51) Int. Cl.
*A61N 1/05*    (2006.01)
*A61B 5/00*    (2006.01)
(Continued)

(52) U.S. Cl.
CPC .......... *A61N 1/36003* (2013.01); *A61B 5/389* (2021.01); *A61B 5/4848* (2013.01);
(Continued)

(58) Field of Classification Search
CPC .............. A61N 1/36003; A61N 1/0551; A61N 1/0558; A61N 1/36062; A61N 1/36153;
(Continued)

(56) References Cited

U.S. PATENT DOCUMENTS

2008/0208287 A1* 8/2008 Palermo ................. A61N 1/323
607/3
2009/0281594 A1* 11/2009 King ................. A61N 1/36139
607/46

FOREIGN PATENT DOCUMENTS

CN    101496748 A    8/2009
CN    207721918 U    8/2018
(Continued)

*Primary Examiner* — Carl H Layno
*Assistant Examiner* — Anh-Khoa N Dinh
(74) *Attorney, Agent, or Firm* — SZDC Law PC

(57) ABSTRACT

A closed-loop spinal cord electrical stimulation system includes a spinal epidural electrical stimulation electrode, a low limb electrical stimulation electrode, a closed-loop electrical stimulator and a controller. The spinal epidural electrical stimulation electrode, the low limb electrical stimulation electrode and the controller are electrically connected to the closed-loop electrical stimulator respectively. The spinal epidural electrical stimulation electrode is used for applying a first electrical stimulation to the spinal epidural site, and the low limb electrical stimulation electrode is used for applying a second electrical stimulation to a low limb. The voltage of the first electric stimulation is 400-600 mV, the voltage of the second electric stimulation is 1 V-1.5 V, and the stimulation frequency of the both is 10-20 Hz. The stimulation system can send electrophysiological signals similar to sensorimotor neural circuitry to the subject with spinal cord injury, and can activate and remodel the neural circuit.

7 Claims, 3 Drawing Sheets

(51) Int. Cl.
*A61B 5/389* (2021.01)
*A61N 1/36* (2006.01)
(52) U.S. Cl.
CPC ......... *A61N 1/0551* (2013.01); *A61N 1/0558* (2013.01); *A61N 1/36062* (2017.08); *A61N 1/36153* (2013.01); *A61N 1/36171* (2013.01); *A61B 2503/40* (2013.01); *A61B 2503/42* (2013.01)
(58) Field of Classification Search
CPC ............ A61N 1/36171; A61N 1/36139; A61N 1/36103; A61N 1/05; A61B 5/389; A61B 5/4848; A61B 2503/40; A61B 2503/42; A61B 5/395; A61B 5/407; A61M 2205/054; A61M 5/14; A61M 5/142; A61M 2210/1085; A61M 5/14276; A61M 5/1723
See application file for complete search history.

(56) References Cited

FOREIGN PATENT DOCUMENTS

| CN | 108744270 | A | 11/2018 |
|----|-----------|---|---------|
| CN | 208877713 | U | 5/2019 |
| CN | 209137753 | U | 7/2019 |
| CN | 110404164 | A | 11/2019 |

\* cited by examiner

CLOSED-LOOP SPINAL CORD ELECTRICAL STIMULATION SYSTEM

This application is the National Stage Application of PCT/CN2020/071041, filed on Jan. 9, 2020, which claims priority to Chinese Patent Application No. 201910809342.0, filed on Aug. 29, 2019, which is incorporated by reference for all purposes as if fully set forth herein.

FIELD OF THE INVENTION

The present invention relates to the field of medical apparatus, and more particularly to a closed-loop spinal cord electrical stimulation system.

DESCRIPTION OF THE RELATED ART

After spinal cord injury, the local circuit below the level of injury still retains the motor functions. Recent studies have shown that the local spinal neural circuit can be activated by spinal epidural electrical stimulation with a certain frequency in combination with body weight supported treadmill training, to facilitate the recovery of motor functions of the low limbs of the experimental animals and the lower limbs of the patients. However, the functional recovery is dependent on the electrical stimulation training, and such recovery of motor functions is temporary. In the existing electrical stimulation training devices, a variety of methods are combined to simulate the closed-loop stimulation, and thus there are a plenty of factors. Currently there is still not a closed-loop electrical stimulation system for spinal cord injury worldwide.

At present, the working principle of the electrical stimulation system for animals and patients after spinal cord injury mainly is that the spinal epidural electrical stimulation is combined with body weight supported treadmill training to enhance the sensory feedback. However, this principle doesn't mean to generate closed-loop stimulation along certain neural circuit in the true sense, and it is dependent on the epidural electrical stimulation and the body weight support treadmill training, and the recovery of motor function will disappear upon the training is stopped. For example, in an existing stimulation system, the paralyzed rats after spinal cord injury are trained by applying epidural electrical stimulation of 40 Hz and 5-HT receptor agonist to the spinal cord segments L2-S1 of rats in combination with the body weight support treadmill training.

In the existing stimulation systems, a body weight supported treadmill is combined for rehabilitation training. However, the body weight supported treadmill has a certain weight-bearing capacity, and can assist the paralyzed lower limbs of the animals or patients after spinal cord injury to produce passive treadmill stepping. This kind of training is not a simple electrical stimulation mode, and thus the characteristics of electrical stimulation signal coding cannot be investigated thoroughly. Meanwhile, the frequency of the spinal epidural electrical stimulation relies on the rehabilitation training methods of the animals and patients, and changes correspondingly when the speed of treadmill changes.

In conclusion, the existing stimulation systems for the animals or patients after spinal cord injury do not simply utilize electrical stimulation to treat the spinal cord injury.

SUMMARY OF THE INVENTION

In order to solve the above technical problems, an object of the invention is to provide a closed-loop spinal cord electrical stimulation system, which can send electrophysiological signals similar to sensorimotor neural circuitry to the subject after spinal cord injury, and can activate and remodel the neural circuit after closed-loop electrical stimulation, thereby facilitating the recovery of motor function of the low limbs of the subject.

For the above purpose, the invention provides a closed-loop spinal cord electrical stimulation system, including a spinal epidural electrical stimulation electrode, a low limb electrical stimulation electrode, a closed-loop electrical stimulator and a controller. The spinal epidural electrical stimulation electrode and the low limb electrical stimulation electrode are connected to the closed-loop electrical stimulator respectively, the controller is electrically connected to the closed-loop electrical stimulator, the spinal epidural electrical stimulation electrode can be implanted into a spinal epidural site of a subject and used for applying a first electrical stimulation to the spinal epidural site, and the low limb electrical stimulation electrode can be implanted into a low limb of the subject and used for applying a second electrical stimulation to the low limb, and the controller is used for sending an electrical stimulation signal to the closed-loop electrical stimulator. The first electrical stimulation has a voltage of 400-600 mV and a frequency of 10-20 Hz, the second electrical stimulation has a voltage of 1 V-1.5 V and a frequency of 10-20 Hz. The time interval between electrical stimulation signals transmitted from the first electrical stimulation and the second electrical stimulation is 50 ms-60 ms.

Preferably, the voltage of the second electrical stimulation is 1 V.

Preferably, the time interval between the second electrical stimulation and the first electrical stimulation is 50 ms.

Preferably, the subject is a mouse.

Preferably, the system also includes an electrical stimulation fixed device for fixing the mouse.

Preferably, the electrical stimulation fixed device includes a base and a mouse trunk fixing unit disposed on the base, the mouse trunk fixing unit includes a height adjustment assembly and a fixing assembly slidably connected on an upper portion of the height adjustment assembly. The height adjustment assembly is used for adjusting the height of the mouse trunk fixing unit in the vertical direction relative to the base, the fixing unit includes a sliding rail slidably connected to the height adjustment assembly and a fixing band secured on the sliding rail for wrapping the abdomen of a mouse.

Preferably, the low limb electrical stimulation electrode can be implanted into anterior tibial muscle of the low limb of the subject.

Preferably, the spinal epidural electrical stimulation electrode can be implanted into the spinal epidural site of the spinal cord segments L2-L4 of the subject.

Preferably, the low limb electrical stimulation electrode includes an I-shaped substrate, a first contact unit and a first interface unit provided on the I-shaped substrate, the first contact unit includes a plurality of electrical stimulation contact points and signal receiving contact points, the first interface unit includes an anode interface, a cathode interface and a ground interface. At least one of the electrical stimulation contact points is electrically connected to the anode interface by a wire and at least one of the electrical stimulation contact points is electrically connected to the cathode interface by a wire to form a stimulation loop. At least one of the signal receiving contact points is electrically connected to the anode interface by a wire and at least one of the signal receiving contact points is electrically connected to the cathode interface by a wire to form a feedback loop. One of the signal receiving contact points is electrically connected to the ground interface by a wire, and a gold foil is provided on the I-shaped substrate for covering the surface of the substrate.

Preferably, the I-shaped substrate has a length of 31-33 mm.

Preferably, there are three electrical stimulation contact points, each electrical stimulation contact point has a diameter of 0.45-0.55 μm, and the distance between two adjacent electrical stimulation contact points is 0.45-0.55 μm.

Preferably, there are multiple layers of I-shaped substrates which are laminated, and the total thickness of the multiple layers of I-shaped substrates is 67-68 μm.

Preferably, each of the anode interface, cathode interface and ground interface include a cover film, the cover films are spaced apart from each other, and a strengthening layer is provided on the cover film.

Preferably, the strengthening layer has a thickness of 0.27-0.33 mm.

Preferably, the spinal epidural electrical stimulation electrode includes a T-shaped substrate having a transverse part and a vertical part, a second interface unit is provided on the transverse part, a second contact unit is provided on the end of the vertical part far away from the transverse part, and a fixed unit is provided on the vertical part for securing the T-shaped substrate to the spine of the mouse. The second interface unit includes an anode interface, a cathode interface and a ground interface. The second contact unit includes a plurality of stimulation contact points arranged sequentially along the extension direction of the vertical part. At least one of the stimulation contact points is connected to the anode interface by a wire, and at least one of the stimulation contact points is connected to the cathode interface by a wire to form a stimulation loop or feedback loop. One of the stimulation contact points is electrically connected to the ground interface by a wire. The fixed unit includes multiple fixing pieces extending along the extension direction of the transverse part and symmetrically arranged along the extension direction of the vertical part. A through hole is opened on the fixing piece for securing the T-shaped substrate which is implanted into the mouse relative to the spine of the mouse. In the invention, the spinal epidural electrical stimulation electrode has the same structure with the electrode in the Chinese patent application 201820803641.4.

Preferably, the first electrical stimulation and the second electrical stimulation are applied to the subject for 1 hour every day, wherein the electrical stimulation is applied every 10 mins, and the electrical stimulation is applied for 15 mins every time.

Preferably, the physiograph (Biopac) is used to detect the electromyographic signals of the subject after the electrical stimulation is applied by the closed-loop spinal cord electrical stimulation system. The physiograph is electrically connected to the controller, and the electromyographic signals detected by the physiograph are detected and processed by the physiograph, to analyze the recovery of the motor function of the subject.

Preferably, the data is processed by using a data processing software, which is preferably Matalab analysis software.

By means of the above technical solutions, the invention has the following advantages:

The invention provides a closed-loop electrical stimulation system suitable to a subject, which combines the spinal epidural electrical stimulation with the low limb electrical stimulation. The system sends electrophysiological signals which simulate the sensorimotor neural circuitry of spinal cord. By means of the first and second electrical stimulation with suitable intensity and frequency, the closed-loop electrical stimulation applied on the subject after spinal cord injury can activate and rebuild the neural circuit, thereby facilitating the recovery of the motor function of the low limbs.

The forgoing description is only used for summarizing the technical solution of the present invention, and in order to more clearly understand the technical means of the present invention and implement the present invention according to the description, preferred embodiments of the present invention are described below in detail in conjunction with the drawings.

Figure 1:
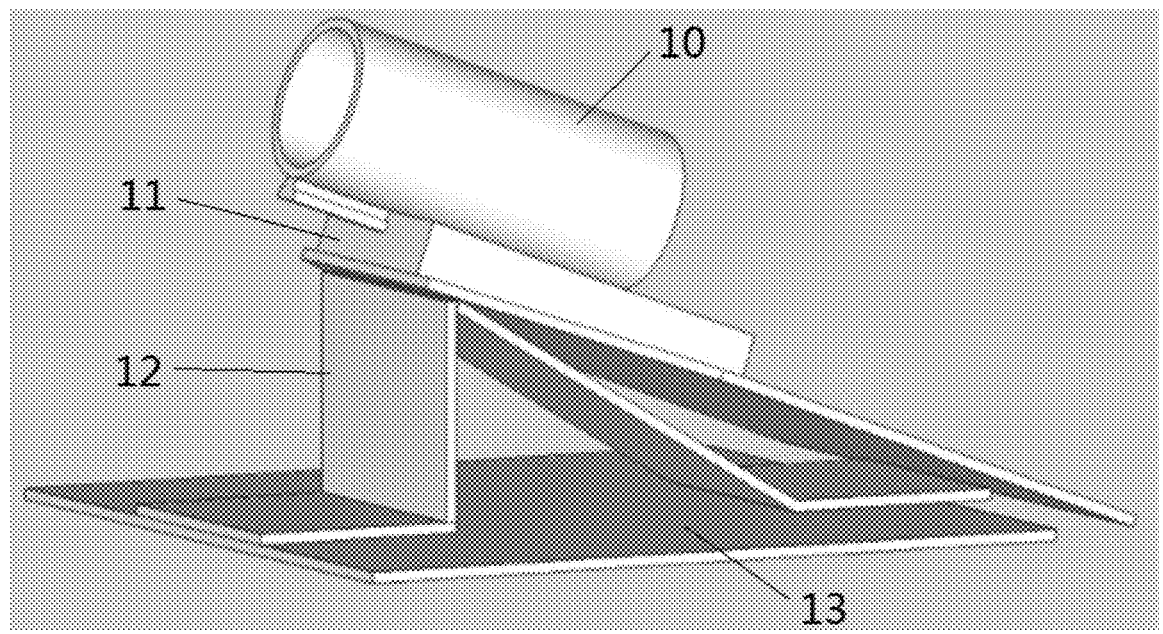
FIG. 1 is a schematic view of the electrical stimulation fixed device according to the invention.

REFERENCE NUMERALS 1. first substrate; 2. electrical stimulation contact point; 3. signal receiving contact point; 4. anode interface; 5. cathode interface; 6. ground interface; 7. gold foil; 8. strengthening layer; 10. fixing band; 11. sliding rail; 12. height adjustment assembly; 13. base.

DETAILED DESCRIPTION OF THE PREFERRED EMBODIMENTS

The present invention will be further described below in conjunction with drawings and specific examples, so that those skilled in the art can better understand and implement the present invention, but the examples described are not intended to limit the present invention.

Example 1

A closed-loop spinal cord electrical stimulation system includes a spinal epidural electrical stimulation electrode, a low limb electrical stimulation electrode, a closed-loop electrical stimulator, an electrical stimulation fixed device for fixing the mouse and a controller. The controller is preferably a computer. The spinal epidural electrical stimulation electrode and the low limb electrical stimulation electrode are connected to the closed-loop electrical stimulator respectively, and the controller is electrically connected to the closed-loop electrical stimulator. The spinal epidural electrical stimulation electrode can be implanted into the spinal epidural site of the spinal cord segments L2-L4 of a subject and used for applying a first electrical stimulation to the spinal epidural site, and the low limb electrical stimulation electrode can be implanted into anterior tibial muscle of low limb of the subject and used for applying a second electrical stimulation to the anterior tibial muscle of low limb. The controller is used for sending an electrical stimulation signal to the closed-loop electrical stimulator. The voltage of the first electrical stimulation is 400-600 mV, and the frequency of the first electrical stimulation is 10-20 Hz. The voltage of the second electrical stimulation is 1 V-1.5 V, and the frequency of the second electrical stimulation is also 10-20 Hz. The second electrical stimulation is applied later than the first electrical stimulation, and the time interval between the first electrical stimulation and the second electrical stimulation is 50 ms-60 ms.

The electrical stimulation fixed device (FIG. 1) includes a base 13 and a mouse trunk fixing unit disposed on the base 13, the mouse trunk fixing unit includes a height adjustment assembly 12 and a fixing assembly slidably connected on the upper portion of the height adjustment assembly 12. The height adjustment assembly 12 is used for adjusting the height of the fixing unit in the vertical direction relative to the base 13. The fixing assembly includes a sliding rail 11 slidably connected to the height adjustment assembly 12 and a fixing band 10 secured on the sliding rail 11 for wrapping the abdomen of a mouse.

Figure 2:
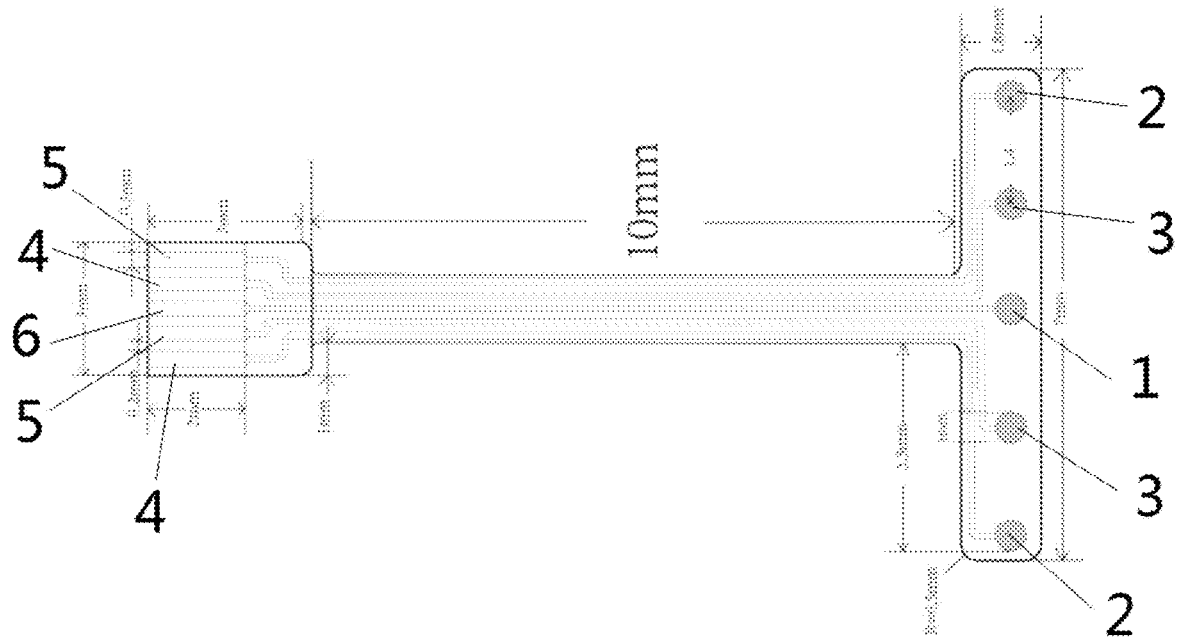
FIG. 2 is a schematic view of the low limb electrical stimulation electrode.
Figure 3:
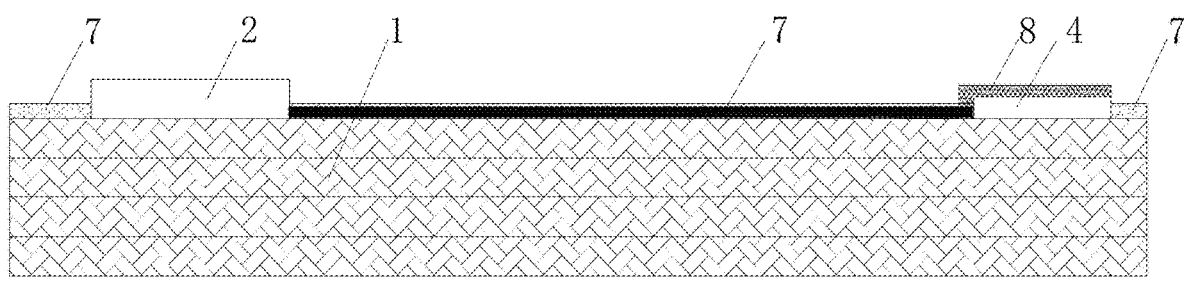
FIG. 3 shows the cross-section view of the low limb electrical stimulation electrode.

The low limb electrical stimulation electrode (FIG. 2-FIG. 3) includes a first substrate 1 for being implanted into the epidural site or the muscle surface of the lower limbs of the mouse, a first contact unit and a first interface unit provided on the first base 1. There are multiple layers of first substrates which are laminated, and the total thickness of the laminated substrates is 58-62 μm. The rigidity of the first substrates can be ensured due to this arrangement mode. The first substrate 1 is I-shaped, and the vertexes of the first substrates 1 are connected with each other by means of a circular arc transition.

The first contact unit includes a plurality of electrical stimulation contact points 2 and signal receiving points 3. The first interface unit includes an anode interface 4, a cathode interface 5 and a ground interface 6. At least one of the electrical stimulation contact points 2 is electrically connected to the anode interface 4 by a wire, and at least one of the electrical stimulation contact points 2 is electrically connected to the cathode interface 5 to form a stimulation loop. At least one of signal receiving contact points 3 is electrically connected to the anode interface 4 by a wire, and at least one of signal receiving contact points 3 is electrically connected to the cathode interface 5 to form a feedback loop. By means of the above arrangement, the electrical stimulation contact points 2 and the signal receiving contact points 3 are electrically connected to the anode interface 4 and the cathode interface 5 respectively, the electrical stimulation is performed on the mouse, and the signals generated from the stimulated mouse can be collected synchronously or asynchronously, and thus the status of the mouse can be observed efficiently in real time. The signal receiving contact points 3 and electrical stimulation contact points 2 are arranged sequentially along the central line direction of the substrate.

The first contact unit disposed on the epidural site of the mouse includes two electrical stimulation contact points 2 and three signal receiving contact points 3. Each electrical stimulation contact point 2 shares a contact terminal with one signal receiving contact point 3. The contact unit provided on the muscle surface of the lower limbs of mouse includes two electrical stimulation contact points 2 and three signal receiving contact points 3. For the signal receiving contact points 3 provided on the epidural site of the mouse and the signal receiving contact points 3 provided on the muscle surface of the lower limbs of the mouse, any one of them is electrically connected to the ground interface 6 by a wire. In the invention, preferably, the middle signal receiving contact point 3 is electrically connected to the ground interface 6. Each of the anode interface 4, the cathode interface 5 and ground interface 6 includes a cover film, and the cover films are spaced apart from each other. A strengthening layer 7 is provided on the cover film, and the thickness of the strengthening layer is 0.27-0.33 mm.

A gold foil 8 is provided on the first substrate 1 for covering the surface of the first substrate 1, the gold foil 8 provides excellent resistance to corrosion and biocompatibility, and thus can guarantee the stability and safety of the implanted substrate for a long time, and can ensure the accuracy of the experimental data effectively.

Figure 4:
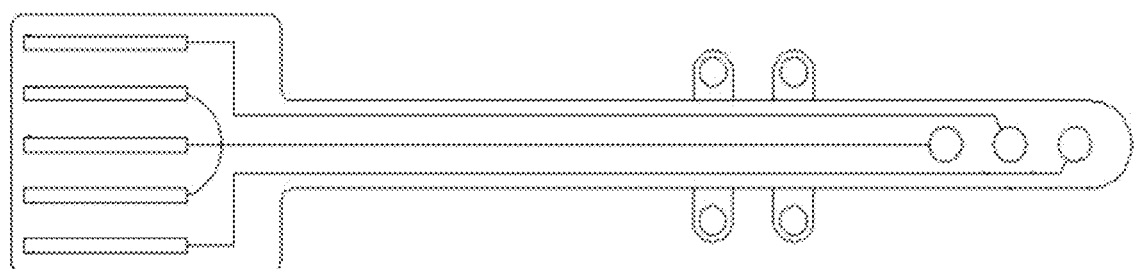
FIG. 4 is a schematic view of the spinal epidural electrical stimulation electrode.

The spinal epidural electrical stimulation electrode (FIG. 4) has the same structure with the electrode in the Chinese patent application number 201820803641.4. The electrode includes a T-shaped substrate which has a transverse part and a vertical part. A second interface unit is provided on the transverse part, a second contact unit is provided on the end of the vertical part far away from the transverse part, and a fixed unit is provided on the vertical part for securing the T-shaped substrate relative to the spine of the mouse. The second interface unit includes an anode interface, a cathode interface and a ground interface. The second contact unit includes a plurality of stimulation contact points arranged sequentially along the extension direction of the vertical part. At least one of the stimulation contact points is connected to the anode interface by a wire, and at least one of the stimulation contact points is connected to the cathode interface by a wire to form a stimulation loop or feedback loop, and wherein one of the stimulation contact points is electrically connected to the ground interface by a wire. The fixed unit includes multiple fixing pieces extending along the extension direction of the transverse part and symmetrically arranged along the extension direction of the vertical part. A through hole is opened on the fixing piece for securing the T-shaped substrate implanted into the mouse relative to the spine of the mouse.

A method for performing a closed-loop spinal cord electrical stimulation by using the closed-loop spinal cord electrical stimulation system is as follows.

1. The spinal epidural electrical stimulation electrode and low limb electrical stimulation electrode are implanted into the spinal epidural site of the spinal cord segments L2-L4 and the anterior tibial muscle of the low limb of the anaesthetic mouse after spinal cord injury respectively, and the wound is sutured after operation.
2. One week after operation, the mouse is fixed on the electrical stimulation fixed device, the electrode nipples of the spinal epidural electrical stimulation electrode and the low limb electrical stimulation electrode are connected to the spinal cord stimulation port and the low limb stimulation port of the closed-loop electrical stimulator. The intensity and the frequency of the first electrical stimulation sent from the spinal epidural electrical stimulation electrode is set to be 400-600 mV, and 10-20 Hz respectively by using a controller (computer), and the low limb electrical stimulation electrode generates the second electrical stimulation 50 ms after the first electrical stimulation, and the second electrical stimulation has an intensity of 1V and a frequency of 10-20 Hz, to provide closed-loop electrical stimulation training for the mouse. The stimulation is performed for 1 h every day, wherein the stimulation is applied every 10 mins, and the stimulation is applied for 15 mins every time.

Figure 5:
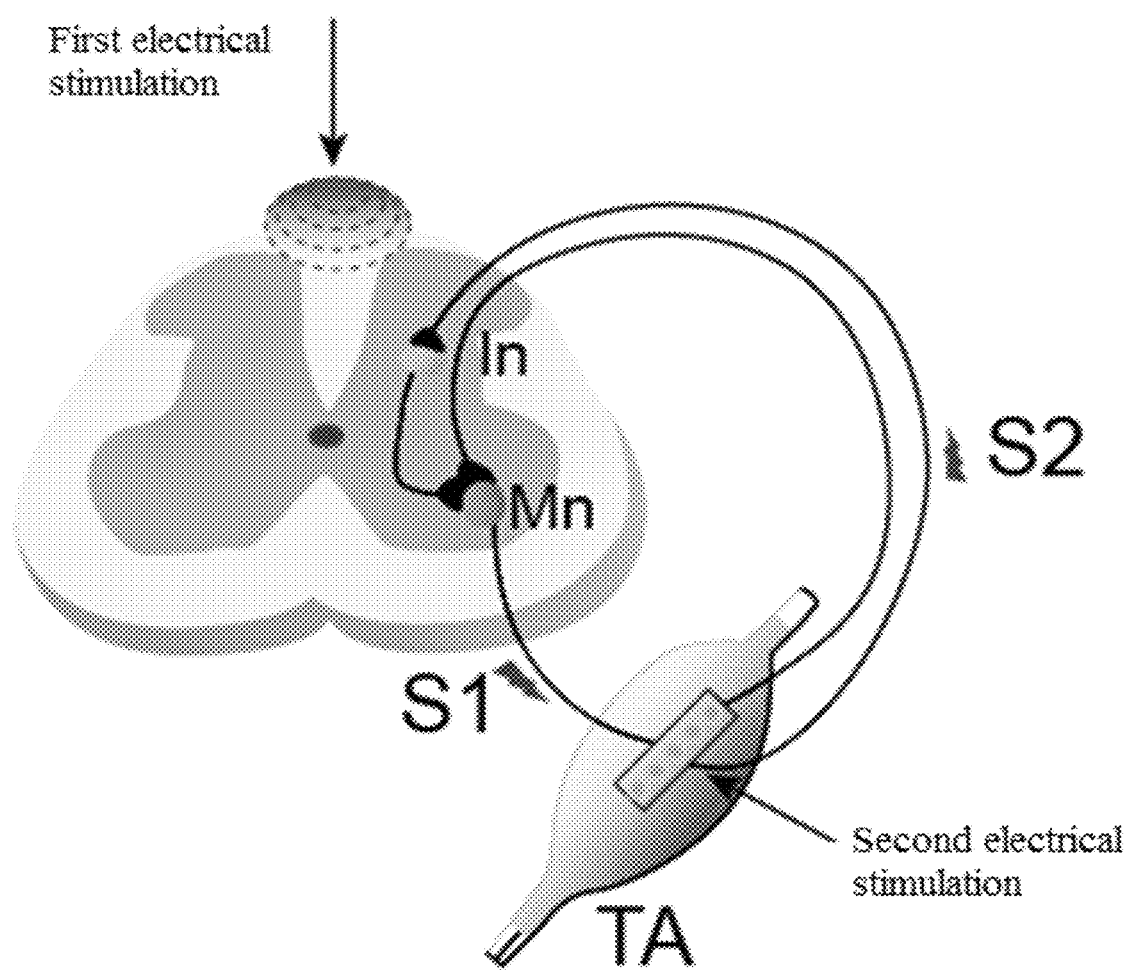
FIG. 5 shows the working principle of applying closed-loop electrical stimulation on the mouse by using the closed-loop spinal cord electrical stimulation system.

FIG. 5 shows the working principle of the above electrical stimulation. In the closed-loop electrical stimulation training, the first electrical stimulation S1 and the second electrical stimulation S2 are applied to the spinal epidural site and the low limb respectively by the closed-loop electrical stimulator, and the intensity of the stimulation S1 and the stimulation S2 can be adjusted respectively by the closed-loop electrical stimulator. During the stimulation training, the mouse is fixed on the mouse fixing unit, and the anterior and posterior limbs of the mouse are suspended to avoid the interference from the limbs. The neural circuit is activated by the low limb electrical stimulation to induce the voluntary movement of the low limbs to enhance the sensory feedback, instead of relying on the body weight supported training apparatus to generate the passive movement. Three weeks after the closed-loop electrical stimulation training at 10-20 Hz, the electromyographic signals of the mouse after spinal cord injury are detected by Biopac, and are transmitted to the computer, and the data is processed by using the software Matalab in the computer. The results show that the closed-loop electrical stimulation applied by the closed-loop spinal cord electrical stimulation system of the invention facilitates the remodeling of the spinal neural circuit.

The description above merely gives the preferred embodiments of the present invention, and is not intended to limit the present invention. It should be noted that several modifications and variations can be made by those of ordinary skill in the art without departing from the technical principles of the invention, and these modifications and variations should be considered within the scope of the present invention.

What is claimed is:

1. A closed-loop spinal cord electrical stimulation system, comprising a spinal epidural electrical stimulation electrode, a low limb electrical stimulation electrode, a closed-loop electrical stimulator and a controller, wherein the spinal epidural electrical stimulation electrode and the low limb electrical stimulation electrode are connected to the closed-loop electrical stimulator respectively, the controller is electrically connected to the closed-loop electrical stimulator, the spinal epidural electrical stimulation electrode can be implanted into a spinal epidural site of a subject and used for applying a first electrical stimulation to the spinal epidural site, and the low limb electrical stimulation electrode can be implanted into a low limb of the subject and used for applying a second electrical stimulation to the low limb, and the controller is used for sending an electrical stimulation signal to the closed-loop electrical stimulator, and wherein the first electrical stimulation has a voltage of 400-600 mV and a frequency of 10-20 Hz, the second electrical stimulation has a voltage of 1 V-1.5 V and a frequency of 10-20 Hz, and the time interval between electrical stimulation signals transmitted from the first electrical stimulation and the second electrical stimulation is 50 ms-60 ms, wherein the low limb electrical stimulation electrode comprises an I-shaped substrate, a first contact unit and a first interface unit provided on the I-shaped substrate; the first contact unit comprises a plurality of electrical stimulation contact points and signal receiving contact points, the first interface unit comprises an anode interface, a cathode interface and a ground interface, wherein at least one of the electrical stimulation contact points is electrically connected to the anode interface by a wire and at least one of the electrical stimulation contact points is electrically connected to the cathode interface by a wire to form a stimulation loop, at least one of the signal receiving contact points is electrically connected to the anode interface by a wire and at least one of the signal receiving contact points is electrically connected to the cathode interface by a wire to form a feedback loop; wherein one of the signal receiving contact points is electrically connected to the ground interface by a wire, and a gold foil is provided on the I-shaped substrate for covering the surface of the substrate.

2. The closed-loop spinal cord electrical stimulation system as claimed in claim 1, wherein the system also comprises an electrical stimulation fixed device for fixing the subject.

3. The closed-loop spinal cord electrical stimulation system as claimed in claim 2, wherein the subject is a mouse, the electrical stimulation fixed device comprises a base and a mouse trunk fixing unit disposed on the base, the mouse trunk fixing unit comprises a height adjustment assembly and a fixing assembly slidably connected on an upper portion of the height adjustment assembly.

4. The closed-loop spinal cord electrical stimulation system as claimed in claim 1, wherein the low limb electrical stimulation electrode can be implanted into anterior tibial muscle of the low limb of the subject.

5. The closed-loop spinal cord electrical stimulation system as claimed in claim 1, wherein the spinal epidural electrical stimulation electrode can be implanted into the spinal epidural site of the spinal cord segments L2-L4 of the subject.

6. The closed-loop spinal cord electrical stimulation system as claimed in claim 1, wherein spinal epidural electrical stimulation electrode comprises a T-shaped substrate which has a transverse part and a vertical part, a second interface unit is provided on the transverse part; a second contact unit is provided on an end of the vertical part far away from the transverse part, and a fixed unit is provided on the vertical part for securing the T-shaped substrate to the spine of the subject, the second interface unit comprises an anode interface, a cathode interface and a ground interface, the second contact unit comprises a plurality of stimulation contact points arranged sequentially along the extension direction of the vertical part, wherein at least one of the stimulation contact points is connected to the anode interface by a wire, and at least one of the stimulation contact points is connected to the cathode interface by a wire to form a stimulation loop or feedback loop, and wherein one of the stimulation contact points is electrically connected to the ground interface by a wire, the fixed unit comprises multiple fixing pieces extending along the extension direction of the transverse part and symmetrically arranged along the extension direction of the vertical part, a through hole is opened on the fixing piece for securing the T-shaped substrate implanted into the subject relative to the spine.

7. The closed-loop spinal cord electrical stimulation system as claimed in claim 1, wherein the first electrical stimulation and the second electrical stimulation are applied to the subject for 1 hour every day, wherein the electrical stimulation is applied every 10 mins, and the electrical stimulation is applied for 15 mins every time.

* * * * *